(12) United States Patent
Abe

(10) Patent No.: US 7,912,293 B2
(45) Date of Patent: Mar. 22, 2011

(54) IMAGE PROCESSING SYSTEM AND IMAGE JUDGMENT METHOD AND PROGRAM

(75) Inventor: Hiroshi Abe, Tokyo (JP)

(73) Assignee: Sony Corporation, Tokyo (JP)

(*) Notice: Subject to any disclaimer, the term of this patent is extended or adjusted under 35 U.S.C. 154(b) by 939 days.

(21) Appl. No.: 11/577,903

(22) PCT Filed: Aug. 31, 2006

(86) PCT No.: PCT/JP2006/317206
§ 371 (c)(1),
(2), (4) Date: Apr. 25, 2007

(87) PCT Pub. No.: WO2007/029592
PCT Pub. Date: Mar. 15, 2007

(65) Prior Publication Data
US 2009/0129681 A1    May 21, 2009

(51) Int. Cl.
*G06K 9/46* (2006.01)
(52) U.S. Cl. .......... 382/194; 382/199; 382/124
(58) Field of Classification Search .......... 382/115, 382/117, 118, 124, 125, 181, 190, 194, 199
See application file for complete search history.

(56) References Cited

U.S. PATENT DOCUMENTS

| 6,392,759 B1* | 5/2002 | Kuwata et al. | 358/1.9 |
| 6,763,125 B2* | 7/2004 | Ohta | 382/104 |
| 7,062,099 B2* | 6/2006 | Li et al. | 382/237 |
| 2001/0036298 A1* | 11/2001 | Yamada et al. | 382/118 |
| 2002/0025079 A1* | 2/2002 | Kuwata et al. | 382/254 |
| 2002/0159616 A1* | 10/2002 | Ohta | 382/104 |
| 2005/0196044 A1* | 9/2005 | Nagahashi et al. | 382/190 |
| 2006/0110009 A1* | 5/2006 | Klassen et al. | 382/112 |

FOREIGN PATENT DOCUMENTS

| JP | 2000-348284 | 2/2000 |
| JP | 2000-180543 | 6/2000 |
| JP | 2004-329825 | 11/2004 |
| JP | 2005-56282 | 3/2005 |

OTHER PUBLICATIONS

International Search Report dated Oct. 3, 2006 (1 pg.).

* cited by examiner

*Primary Examiner* — Jon Chang
(74) *Attorney, Agent, or Firm* — K&L Gates LLP

(57) ABSTRACT

An image processing system and image judgment method able to suitably judge whether or not an image includes an image of a predetermined subject to be captured as the image and a program run in the image processing system are provided. Edges of a captured image are enhanced, and an evaluation value Ev concerning intensities of edges and/or amounts of edges included in the captured image is acquired based on values of pixels included in this edge enhanced image. It is judged whether or not the captured image includes an image of a predetermined subject FG based on this acquired evaluation value Ev. It becomes possible to accurately judge if the captured image includes an image of the predetermined subject FG. Further, it is also possible to judge if the image of that subject FG is suitable for a predetermined purpose (for example a template use image of biometric authentication) in accordance with the evaluation value Ev.

20 Claims, 11 Drawing Sheets (A)

(B)

(C)

(A)

(B)

(C)

(A)

(B)

(C)

(D)

(A)

(B)

(C)

(D)

IMAGE PROCESSING SYSTEM AND IMAGE JUDGMENT METHOD AND PROGRAM

CROSS REFERENCE TO RELATED APPLICATIONS

The present application claims priority to Japanese Patent Document No. 2005-257858 filed on Sep. 6, 2005, the disclosure of which is herein incorporated by reference.

BACKGROUND

The present invention relates to an image processing system for judging whether or not an image includes an image of a predetermined subject to be captured as the image and an image judgment method and a program of the same.

The present invention for example relates to an image processing system for judging whether or not an image captured for biometric authentication includes an image of a biometric feature.

Along with the advances made in information communications utilizing networks, higher security personal authentication systems are being demanded.

Biometric authentication judges whether or not a person to be authenticated is a true registered person based on information obtained from physical characteristics of the person, for example, a fingerprint, voice print, retinal pattern, and vein pattern of the finger. Consequently, biometric authentication can greatly reduce the instances of another person pretending to be the true registered person.

Japanese Patent Publication (A) No. 2004-329825 discloses a system for authenticating a person by emitting a near-infrared ray and capturing the image of a pattern of blood vessels of the finger, and comparing this with a previously registered pattern of the blood vessels.

Problem to be Solved by the Invention

When authenticating a person based on an image of a biometric feature, it is necessary to capture the biometric image of the true person first, extract the information required for identifying the person from that, and register this as the authentication information in a suitable system. The information of the biometric feature acquired for the authentication will be called a "template" below.

Since a person is authenticated based on this template, when the template-use image does not include a suitable image indicating the physical characteristics of the registered person, for example, the pattern of the blood vessels, the reliability of the authentication is remarkably lowered. For example, when registering an image of the pattern of blood vessels of the finger as the template, if erroneously registering the image of a portion other than the finger, it suffers from the inconvenience that the true registered person will not pass the authentication or a completely different person will pass the authentication.

Whether or not the acquired template is suitable is checked visually by for example a manager of the authentication information. However, with visual checks, it suffers from inconvenience that the reliability of authentication cannot be stably maintained due to the variation of judgment of persons. Further, when processing a large amount of authentication information, with the method of visually checking template-use images one by one, it also suffers from the disadvantage that the work efficiency becomes very low.

Due to the above, it has been desired to provide an image processing system and an image judgment method able to suitably judge whether or not an image includes an image of a predetermined subject to be captured as the image and a program run in such an image processing system.

SUMMARY

Means for Solving the Problem

An image processing system according to a first embodiment of the present invention has an edge enhancement unit configured to enhance edges of an image, an evaluation value acquisition unit configured to acquire an evaluation value concerning intensities of edges and/or amounts of edges included in the image based on values of pixels included in the image with edges enhanced at the edge enhancement unit, and a judgment unit configured to judge whether or not the image includes an image of a predetermined subject to be captured as the image based on the evaluation value acquired by the evaluation value acquisition unit.

According to the image processing system according to the first embodiment, the edge enhancement unit enhances the edges of the image. The evaluation value acquisition unit acquires the evaluation value concerning the intensities of edges and/or amounts of edges included in the image based on values of pixels included in the edge enhanced image. Then, the judgment unit judges whether or not the image includes an image of the predetermined subject based on the acquired evaluation value.

The evaluation value acquisition unit may also acquire the evaluation value based on for example a sum of values of all pixels included in the image enhanced in edges at the edge enhancement unit.

Alternatively, it may acquire the evaluation value based on the sum of values of pixels having intensities of edges exceeding a predetermined threshold value among all pixels included in the image with edges enhanced at the edge enhancement unit.

Alternatively, it may acquire the evaluation value based on a number of pixels having intensities of edges exceeding a predetermined threshold value among all pixels included in the image with edges enhanced at the edge enhancement unit.

Alternatively, it may acquire the evaluation value based on the value of the pixel having the highest edge intensity among all pixels included in the image with edges enhanced at the edge enhancement unit.

The image processing system according to the first embodiment may further have a contour detection unit configured to detect contours of the subject from the image and a region specifying unit configured to specify a region inside from the contours detected at the contour detection unit. In this case, the evaluation value acquisition unit may acquire the evaluation value based on values of pixels included in the region specified at the region specifying unit in the image with edges enhanced at the edge enhancement unit.

Due to this, the evaluation value is acquired based on the values of pixels included in the region inside from the contours of the subject.

Further, the edge enhancement unit may sequentially enhance edges of images acquired at the image acquisition unit, and the evaluation value acquisition unit may sequentially acquire evaluation values of images acquired at the image acquisition unit. In this case, the judgment unit may include a first judgment unit for comparing evaluation values of images sequentially acquired at the image acquisition unit and a first threshold value and judging whether or not intensities of edges and/or amounts of edges included in the acquired images reach a first reference level based on the comparison results and a second judgment unit for determining a second threshold value for determining a second reference level exceeding the first reference level based on evaluation values of a predetermined number of images judged to reach the first reference level in the first judgment unit when the predetermined number of images are continuously acquired, comparing the evaluation value of any one of the predetermined number of images or an image acquired following the predetermined number of images and the second threshold value, and judging whether or not the image compared includes an image of the subject based on the comparison result.

Further, the judgment unit may include a third judgment unit configured to compare evaluation values sequentially acquired at the evaluation value acquisition unit and a third threshold value for determining a third reference level exceeding the second reference level and judge whether or not the image compared includes an image of the subject based on the comparison result.

According to above configuration, the first judgment unit compares sequentially acquired evaluation values of images and a first threshold value and sequentially judges whether or not intensities of edges and/or amounts of edges included in the acquired images reach a first reference level based on the comparison results. The second judgment unit determines a second threshold value for determining a second reference level exceeding the first reference level based on evaluation values of a predetermined number of images judged to reach the first reference level in the first judgment unit when the predetermined number of images are continuously acquired. It compares the evaluation value of any one of the predetermined number of images or an image acquired following the predetermined number of images and the second threshold value and judges whether or not the image compared includes an image of the subject based on the comparison result.

On the other hand, the third judgment unit compares evaluation values sequentially acquired at the evaluation value acquisition unit and a third threshold value for determining a third reference level exceeding the second reference level and judges whether or not the image compared includes an image of the subject based on the comparison result.

The image processing system according to the first embodiment may further have an information output unit configured to output information concerning the evaluation values of images sequentially acquired at the image acquisition unit. The information output unit may output the information in accordance with the number of continuously acquired images judged to reach the first reference level at the first judgment unit.

A second embodiment of the present invention relates to an image judgment method for judging whether or not an image includes an image of a predetermined subject to be captured as the image. This image judgment method has a first step of enhancing the edges of the image, a second step of acquiring an evaluation value concerning intensities and/or amounts of edges included in the image based on values of pixels included in the image with edges enhanced in the first step, and a third step of judging whether or not the image includes an image of the subject based on the evaluation value acquired in the second step.

According to the image judgment method according to the second embodiment, the first step enhances edges of the image and the second step acquires an evaluation value concerning intensities and/or amounts of edges included in the image based on values of pixels included in the edge enhanced image. Then, the third step judges whether or not the image includes an image of the subject based on the acquired evaluation value.

A third embodiment of the present invention relates to a program of an image processing system including a computer for judging whether or not an image includes an image of a predetermined subject to be captured as the image. It makes the image processing system execute a first step of enhancing edges of the image, a second step of acquiring an evaluation value concerning intensities of edges and/or amounts of edges included in the image based on values of pixels included in an image with edges enhanced at the first step, and a third step of judging whether or not the image includes an image of the subject based on the evaluation value acquired in the second step.

According to the program according to the third embodiment, in the first step, the edges of the image are enhanced by the image processing system. In the second step, based on the values of the pixels included in the edge enhanced image, an evaluation value concerning the intensities and/or amounts of edges included in the image is acquired by the image processing system. Then, in the third step, based on the acquired evaluation value, whether or not the image of the subject is included in the image is judged by the image processing system.

EFFECTS OF THE INVENTION

According to the present invention, by converting the intensities and/or amounts of edges included in an image into a numerical value as an evaluation value, it is possible to suitably judge whether or not that image includes an image of a predetermined subject to be captured as the image without depending upon vague human judgment.

Additional features and advantages of the present invention are described in, and will be apparent from, the following Detailed Description and the Figures.

DESCRIPTION OF NOTATIONS

10 . . . control unit, 20 . . . light source, 30 . . . optical system, 40 . . . image capturing unit, 50 . . . image display unit, 60 . . . operation unit, 70 . . . storage unit, 101 . . . image acquisition unit, 102 . . . contour detection unit, 103 . . . region specifying unit, 104 . . . edge enhancement unit, 105 . . . evaluation value acquisition unit, 106 . . . judgment unit, 1061 . . . first judgment unit, 1062 . . . second judgment unit, 1063 . . . third judgment unit, 107 . . . registration unit, 108 . . . comparison unit, and 109 . . . display processing unit.

DETAILED DESCRIPTION

Figure 1:
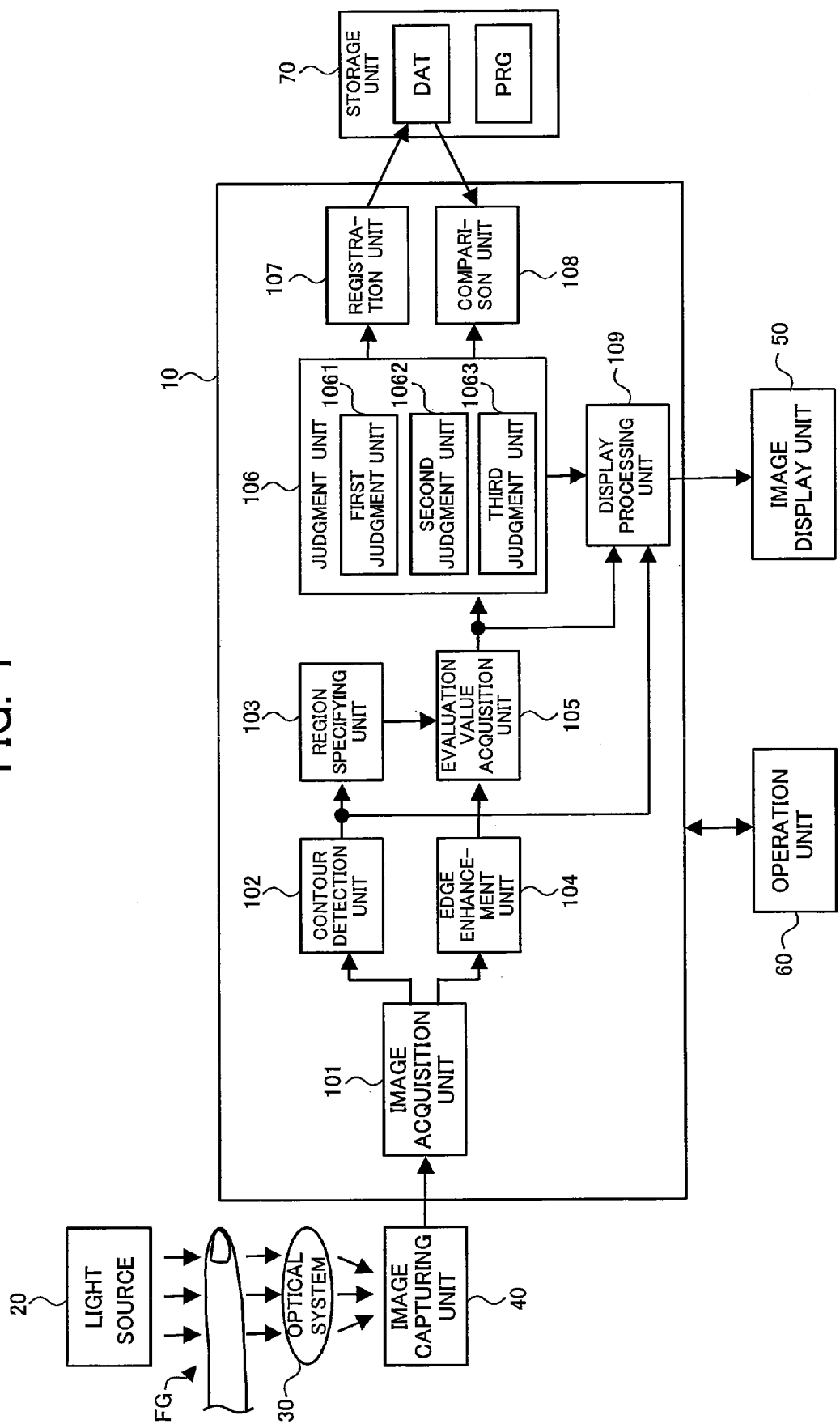
FIG. 1 is a diagram showing an example of the configuration of an image processing system according to an embodiment of the present invention.

FIG. 1 is a diagram showing an example of the configuration of an image processing system according to an embodiment of the present invention.

The image processing system shown in FIG. 1 has a control unit 10, light source 20, optical system 30, image capturing unit 40, image display unit 50, operation unit 60, and storage unit 70.

The light source 20 generates light to irradiate a subject to be captured as an image FG (human finger in the example of FIG. 1). This light is for example near infrared light having a wavelength of about 600 nm to 1300 nm and by nature has a relatively high transmission property with respect to human tissue and is characteristically absorbed by the hemoglobin in the blood.

The light source 20 is configured by for example a light emitting diode, halogen lamp, etc.

The optical system 30 guides the light passed through the subject FG to a light receiving surface of the image capturing unit 40. In the image of the subject FG projected onto the light receiving surface of the image capturing unit 40, a portion having a thicker blood vessel becomes darker.

The image capturing unit 40 captures the image of the subject FG projected onto the light receiving surface, converts this to image data, and outputs the data to the control unit 10. The image capturing unit 40 is configured by for example a CCD (charge coupled device) or CMOS (complementary metal oxide semiconductor) sensor or other imaging device.

The control unit 10 controls the overall operation and various types of signal processing of the image processing system. For example, it controls the generation of the light at the light source 20, the capturing of the image in the image capturing unit 40, the display of the image in the image display unit 50, and so on in response to an instruction of a user input from the operation unit 60. Further, it performs various types of image processing concerning biometric authentication such as processing for judging whether or not the image captured by the image capturing unit 40 includes an image of the predetermined subject, processing for registering a template prepared based on the captured image in the storage unit 70, and processing for comparing the captured image and the template.

The control unit 10 is configured by for example a computer and executes the above control and signal processing based on a program PRG stored in the storage unit 70.

The image display unit 50 displays an image in accordance with the display data supplied from the control unit 10. For example, it displays information concerning the template use image in accordance with the display data supplied from the display processing unit 109 explained later.

The operation unit 60 is an interface for inputting the instructions of the user and is configured by for example keys, buttons, dials, a touch panel, a mouse, and other input devices.

The storage unit 70 stores the program PRG to be run by the computer of the control unit 10 and a template DAT. Further, it stores constant data utilized in the processing of the control unit 10, variable data which must be temporarily held in the processing step, and so on.

The storage unit 70 is configured by for example a RAM (random access memory), ROM (read only memory), non-volatile memory, hard disc, or other storage device.

Components of the control unit 10 will be explained next.

The control unit 10 shown in FIG. 1 has, as functional components concerning the image processing, an image acquisition unit 101, contour detection unit 102, region specifying unit 103, edge enhancement unit 104, evaluation value acquisition unit 105, judgment unit 106, registration unit 107, comparison unit 108, and display processing unit 109.

The image acquisition unit 101 is an embodiment of the image acquisition unit and image acquiring means of the present invention.

The contour detection unit 102 is an embodiment of the contour detection unit and contour detecting means of the present invention.

The region specifying unit 103 is an embodiment of the region specifying unit and region specifying means of the present invention.

The edge enhancement unit 104 is an embodiment of the edge enhancement unit and edge enhancement means of the present invention.

The evaluation value acquisition unit 105 is an embodiment of the evaluation value acquisition unit and evaluation value acquiring means of the present invention.

The judgment unit 106 is an embodiment of the judgment unit and judging means of the present invention.

The image acquisition unit 101 sequentially acquires images captured by the image capturing unit 40. Namely, when the registration processing of a template and the comparison processing are started in response to an instruction input from the operation unit 60, the image acquisition unit 101 controls the operations of the light source 20 and the image capturing unit 40 to thereby irradiate the subject FG with near infrared light, sequentially captures the projected images, and sequentially fetches the data of the captured images.

The edge enhancement unit 104 enhances the edges of the images acquired by the image acquisition unit 101.

For the enhancement of the edges of an image, there is used for example a Gaussian filter, a Laplacian filter, or other image filter. Namely, after eliminating a noise component included in the image by the Gaussian filter, the changes of pixel values are enhanced by the Laplacian filter. Due to this, the point shaped noise components included in the image are eliminated, and the line shaped edge components are enhanced.

Figure 2:
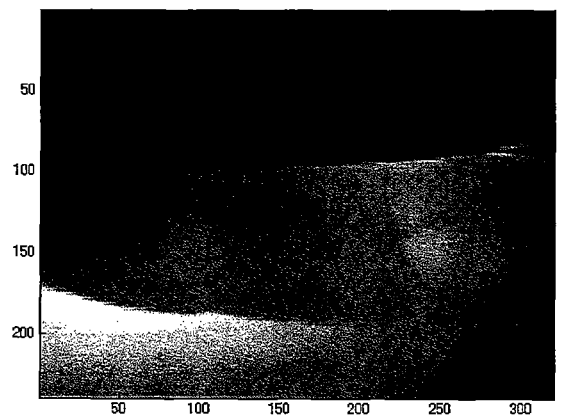
FIGS. 2(A) to 2(C) are diagrams showing a first example of results obtained by applying edge enhancement to a captured image.
Figure 2:
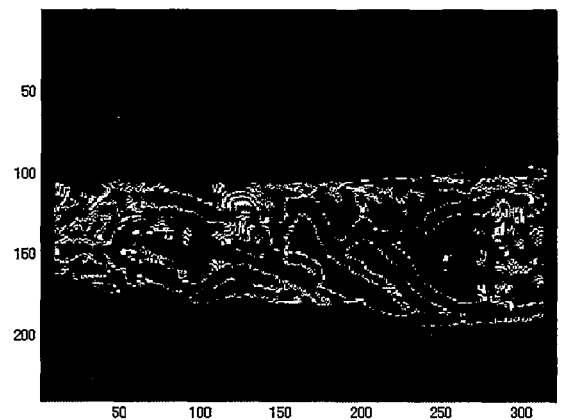
Figure 2:
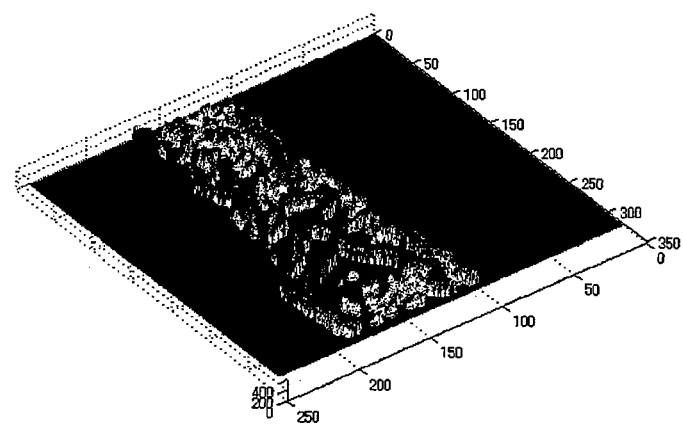

FIGS. 2(A) to 2(C) are diagrams showing an example of results of applying edge enhancement by the Gaussian filter and Laplacian filter explained above with respect to a captured image of the subject FG.

FIG. 2(A) shows the image before the edge enhancement, and FIG. 2(B) shows the image after the edge enhancement. Further, FIG. 2(C) is a diagram illustrating the pixel values of the image shown in FIG. 2(B) in three dimensions.

As seen from the example of FIGS. 2(A) to 2(C), when edge enhancement is applied to an image captured by the image capturing unit 40, the pixel values of the blood vessel (particularly the vein) portions of the finger stick out in comparison with the other portions.

Both of the image before the edge enhancement shown in FIG. 2(A) and the image after the edge enhancement shown in FIGS. 2(B) and 2(C) have sign-less 8-bit pixel values. When an image having 8-bit pixel values is processed by the Gaussian filter and the Laplacian filter, the pixel values after that processing may become values exceeding 8 bits. However, in the example of FIGS. 2(B) and 2(C), the pixel values after processing are limited to 8 bits, therefore the blood vessels of the original image shown in FIG. 2(A) and the blood vessels of the image after the edge enhancement shown in FIG. 2(B) do not coincide in their visual intensities that much. Namely, both of the blood vessels which are thin and light and the blood vessels which are thick and dark become almost the same in intensities in the image after the edge enhancement.

Figure 3:
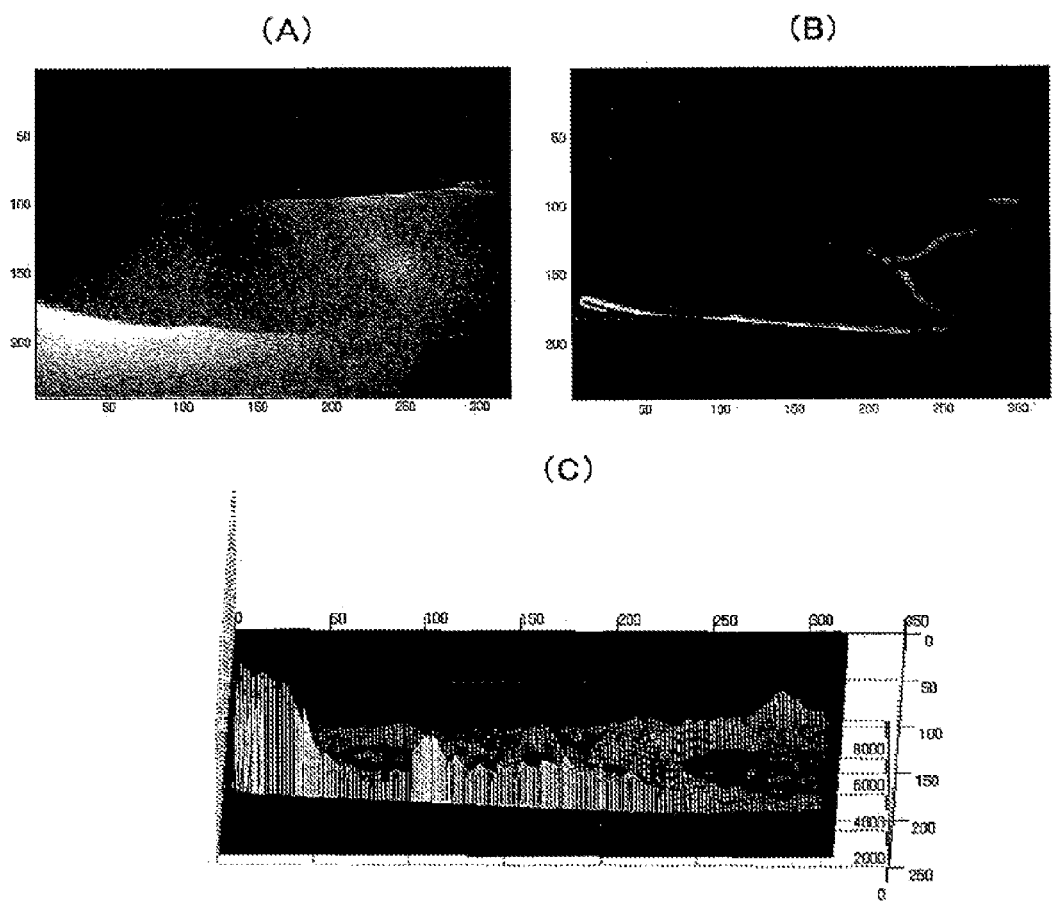
FIGS. 3(A) to 3(C) are diagrams showing a second example of results obtained by applying edge enhancement to a captured image.

On the other hand, FIGS. 3(A) to 3(C) are diagrams showing a second example of results of applying the same edge enhancement by the Gaussian filter and the Laplacian filter. The difference from the first example shown in FIGS. 2(A) to 2(C) resides in that the bit restriction on the pixel values after the edge enhancement is abolished. FIG. 3(A) shows the image before the edge enhancement, and FIGS. 3(B) and 3(C) show images after the edge enhancement.

As seen from the comparison of FIGS. 2(A) to 2(C) and FIGS. 3(A) to 3(C), when the bit restriction on the pixel values is abolished, the difference of dark/light in the original image sensitively appears in the image after the edge enhancement. The pixel values of the dark blood vessels become large, and the pixel values of the thin blood vessels become small.

In order to register the information of the blood vessels as a template, the image of the stable blood vessels which can be sufficiently used for authentication must be extracted. Accordingly, the image captured by the image capturing unit 40 desirably includes many images of blood vessels which are as thick and dark as possible.

Therefore, the edge enhancement unit 104 abolishes the bit restriction for example as shown in the images of FIGS. 2(A) to 2(C) and sets the bit lengths of the pixel values after the edge enhancement to the suitable lengths. Due to this, an evaluation value Ev acquired in the evaluation value acquisition unit 105 explained later becomes a value more suitably expressing whether or not this is an image suitable for a template.

However, when abolishing the bit restriction of the pixel values after the edge enhancement, an image correctly reflecting the darkness/lightness of the blood vessels is obtained as explained above, but as shown in FIGS. 3(B) and 3(C), also the edges of the contour portions of the finger which are unnecessary as a template are enhanced. Particularly when the background of the subject FG is bright, these contours appear stronger than the blood vessels. When the contours are enhanced too much, even if a mask for correctly cutting out the subject FG along the contours is prepared, the influence of the contours reaches the portion further inside the contours, therefore the reliability of the evaluation value Ev explained later is lowered.

Therefore, in the contour detection unit 102 and region specifying unit 103 explained next, a mask for reliably cutting out the region inside from the contours of the finger is prepared so that the evaluation value Ev is acquired in the state eliminating the influence of the contour portions.

The contour detection unit 102 detects the contours of the subject FG from the image captured by the image capturing unit 40. For example, the contours of the subject FG are detected according to the method of extracting the edge portions of the captured image by using an appropriate differential operator and a method of binary processing the captured image so that the subject FG and the background are separated by an appropriate threshold value.

The region specifying unit 103 specifies the region inside from the contours detected by the contour detection unit 101 and prepares a mask for cutting out this specified region from the image after the edge enhancement.

Figure 4:
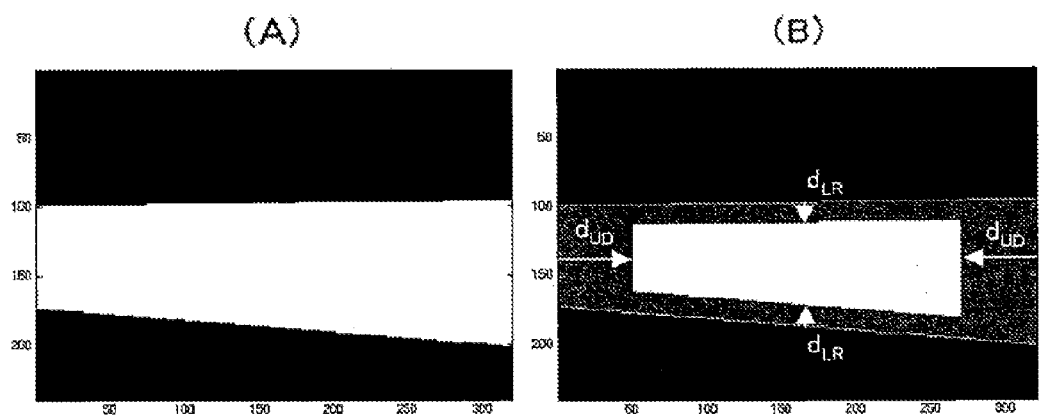
FIGS. 4(A) and 4(B) are diagrams showing an example of detecting contours of a subject from the captured images shown in FIGS. 2(A) to 2(C) and FIGS. 3(A) to 3(C) and specifying regions inside those.

FIGS. 4(A) and 4(B) are diagrams showing an example of detecting the contours of the subject FG from the captured images shown in FIGS. 2(A) to 2(C) and FIGS. 3(A) to 3(C) and specifying the region inside from that.

FIG. 4(A) shows an example of the contours of the subject FG detected by the contour detection unit 102. The black portions of FIG. 4(A) indicate the background of the subject FG, and the white portion indicates the inside of the subject FG. Further, a white/black boundary corresponds to a contour detected at the contour detection unit 102.

FIG. 4(B) shows an example of the region inside from the subject FG specified by the region specifying unit 103. The white portion of FIG. 4(B) indicates the inside region of the subject FG specified in the region specifying unit 103. Further, a gray portion indicates the inside of the contours detected by the contour detection unit 102 and the portion which is excluded from the region specified in the region specifying unit 103.

In the example of FIGS. 4(A) and 4(B), the contours of the subject FG are comprised of a top, bottom, left, and right, that is, four sides. When the contours of the subject FG are comprised of a plurality of sides in this way, the region specifying unit 103 moves for example these sides to the inside of the contour by predetermined distances. Then, it specifies the region enclosed by the sides after movement as the inside region of the subject FG. In the example of FIG. 4(B), the upper side is moved in the downward direction of the image by exactly a distance dLR, and the lower side is moved in the upward direction of the image by exactly the distance dLR. At the same time, the side on the left is moved in the rightward direction of the image by exactly a distance dUD, and the side on the right is moved in the leftward direction of the image by exactly the distance dUD. Then, the region enclosed by the four sides after movement is specified as the region inside from the contours of the subject FG.

The region specified by the region specifying unit 103 in this way is reliably separated from the contours of the subject FG. For this reason, even in a case where the pixel values of the contours are abnormally high as shown in FIGS. 3(B) and 3(C), almost no influence thereof is exerted upon the inside of the region. Accordingly, when only the region specified by the region specifying unit 103 is cut out from the image after the edge enhancement by masking, an image of just the blood vessels from which the influence of the contours is eliminated can be obtained.

When cutting out the portion inside the contours of the subject FG by the masking as explained above, the image of the blood vessels existing in the vicinity of the contours is eliminated from the coverage when finding the evaluation value Ev. Namely, a portion of the information of the blood vessels will be lost. However, the image of the blood vessels existing in the vicinity of the contours easily changes in accordance with the method of placing the finger and no longer appears in the captured image if just rotating the finger a little. The image of such blood vessels is originally an image not suitable for registration of a template, therefore there is no inconvenience even when the evaluation value Ev is found from the result by eliminating this by the masking.

The evaluation value acquisition unit 105 acquires the evaluation value Ev concerning the intensities and/or amounts of the edges included in the image input from the image capturing unit 40 based on the values of the pixels included in the image with edges enhanced by the edge enhancement unit 104. For example, it calculates the sum of the values of all pixels included in the image after the edge enhancement and acquires this as the evaluation value Ev.

Note that the evaluation value acquisition unit 105 according to the present embodiment acquires the evaluation value Ev based on the values of the pixels included in the internal region of the subject FG specified in the region specifying unit 103 among all pixels included in the image after the edge enhancement and does not utilize the values of pixels out of this region at the time of determination of the evaluation value Ev. Namely, it acquires the evaluation value Ev based on the pixel values of the region inside from the contours cut out by the mask prepared by the region specifying unit 103.

Figure 5:
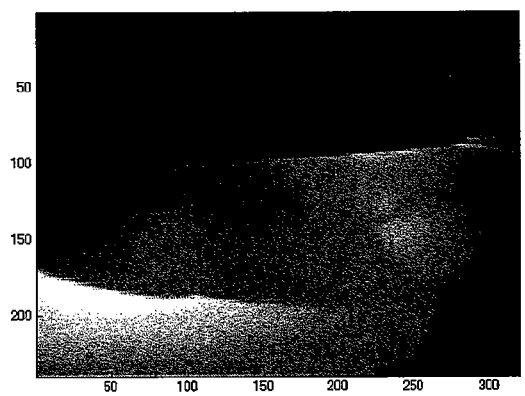
FIGS. 5(A) to 5(C) are diagrams showing an example of cutting out a region inside from the contours shown in FIG. 4(B) from the image after the edge enhancement shown in FIG. 3(B) by masking.
Figure 5:
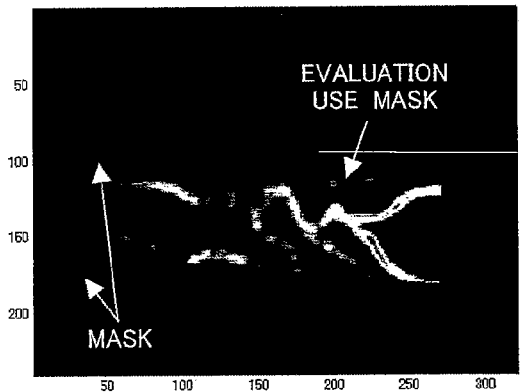
Figure 5:
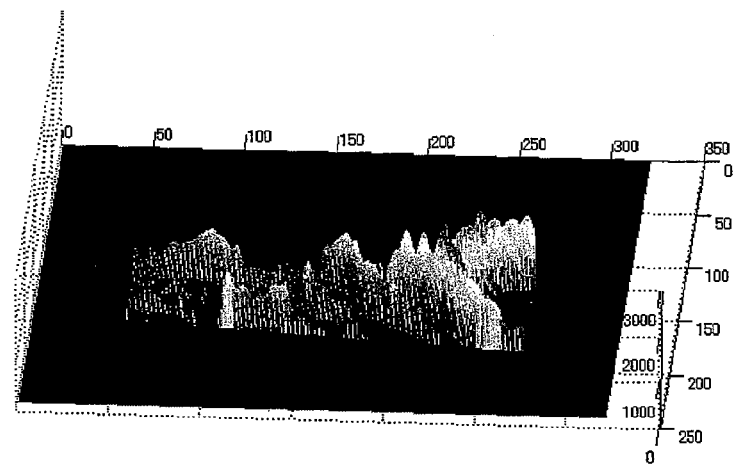

FIGS. 5(A) to 5(C) are diagrams showing an example of cutting out the region inside from the contours shown in FIG. 4(B) from the image after the edge enhancement shown in FIG. 3(B) by the masking.

FIG. 5(A) shows the image before the edge enhancement, and FIGS. 5(B) and 5(C) show images obtained by cutting out only the region inside from the contours from the image after the edge enhancement by the masking.

When cutting out only the region specified in the region specifying unit 103 from the image after the edge enhancement, the influence of the contours of the subject FG is eliminated as shown in the images of FIGS. 5(B) and 5(C). Only the image of the blood vessels existing inside of the subject FG stands out. This image of blood vessels greatly changes in the values of the pixels in accordance with the thickness and darkness of the blood vessels in the original image.

The evaluation value acquisition unit 105 calculates the sum of the pixel values in the image suitably reflecting the dark/light state of the blood vessels in this way as the evaluation value Ev. This evaluation value Ev becomes a value indicating the characteristics of the subject FG suitable as the template use image.

FIGS. 6(A) to 6(D) are diagrams showing an example of a case where the image captured by the image capturing unit 40 includes the subject FG and a case where it does not.

Figure 6:
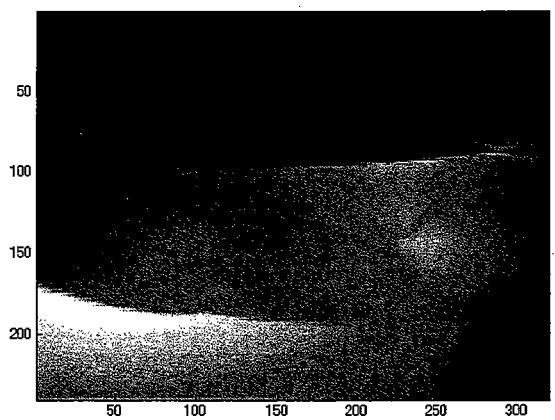
FIGS. 6(A) to 6(D) are diagrams showing an example of a case where the captured image includes the predetermined subject and a case where it does not.
Figure 6:
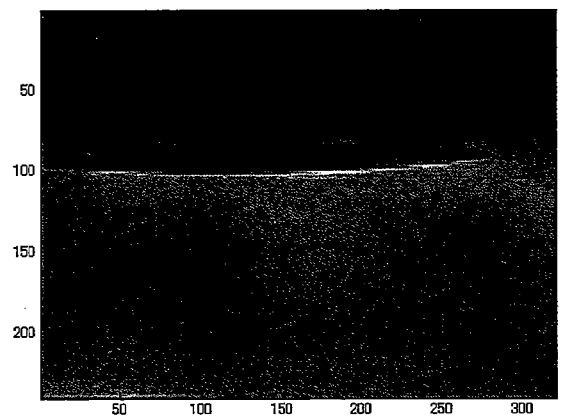
Figure 6:
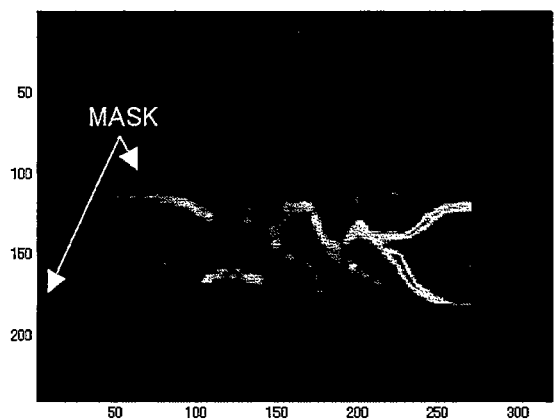
Figure 6:
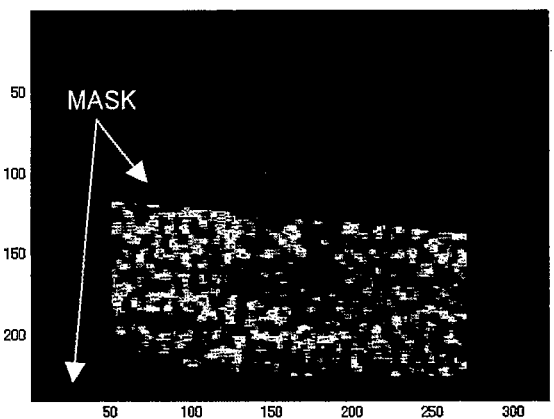

FIG. 6(A) shows the captured image including the subject FG, and FIG. 6(C) shows the image after applying the edge enhancement and masking to the image shown in this FIG. 6(A).

FIG. 6(B) shows the captured image not including the subject FG, and FIG. 6(D) shows the image after applying the edge enhancement and masking to the image shown in this FIG. 6(B).

The blood vessels inside the finger are beautifully projected in the image of FIG. 6(A), therefore, in the image of FIG. 6(C) after applying the edge enhancement and masking to this, strong edges are locally concentrated at the portions of the blood vessels. On the other hand, no image of blood vessels is projected in the image shown in FIG. 6(B), and it is poor in darkness/lightness, therefore, in the image of FIG. 6(D) after applying the edge enhancement and masking to this, weak edges are scattered overall, and no clear edges corresponding to the image of the blood vessels appear.

When comparing the sums of the pixel values of the two, the sum of the image of FIG. 6(C) becomes "2434244", and sum of the image of FIG. 6(D) becomes "1177685". In this way, there is a large difference in the sum of pixel values between the case where the subject FG is included and the case where it is not included. Accordingly, the evaluation value Ev acquired by the evaluation value acquisition unit 105 (namely the sum of the pixel values of image subjected to the edge enhancement and masking) can express the presence/absence of the subject FG according to the difference of the values.

When comparing FIG. 6(C) and FIG. 6(D), the image not including the subject FG includes more pixels having small pixel values (that is, weak edges) and less pixels having large pixel values (that is, strong edges) in comparison with the image including the subject FG. Therefore, the evaluation value acquisition unit 105 need not just add up all the pixel values, but may also add up only pixel values larger than a certain threshold value and acquire the sum as the evaluation value Ev. Namely, the evaluation value Ev may be acquired based on the sum of values of pixels having edge intensities exceeding a predetermined threshold value among all pixels included in the image with edges enhanced in the edge enhancement unit 104 (note, in the region specified by the region specifying unit 103). Due to this, the difference of evaluation value Ev between the case where the subject FG is included and the case where it is not included can be made further conspicuous.

Figure 7:
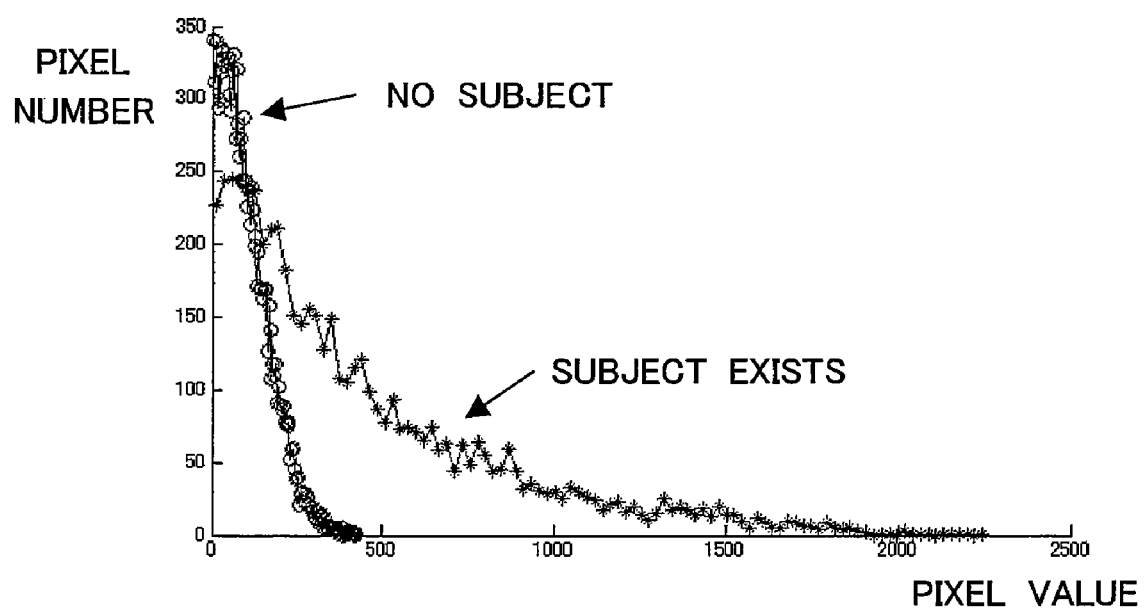
FIG. 7 is a diagram comparing a distribution of pixel values in a captured image including the subject shown in FIG. 6(C) and a distribution of pixel values in a captured image not including the subject shown in FIG. 6(D).

FIG. 7 is a diagram comparing a distribution of pixel values in the image shown in FIG. 6(C) (case including the subject FG) and a distribution of pixel values in the image shown in FIG. 6(D) (case not including the subject FG). An abscissa indicates pixel values, and an ordinate indicates pixel numbers.

As shown in FIG. 7, when the captured image does not include the subject FG, in the image after applying the edge enhancement and masking, most pixels are distributed within a range smaller than a constant pixel value ("500" in the example of FIG. 7). On the other hand, when the captured image includes the subject FG, the pixels are distributed within a wide range from the small pixel value to the large pixel value.

FIGS. 8(A) to 8(D) are diagrams comparing the case where pixel values of the threshold value or less are made zero and the case where they are not made zero in the image after the edge enhancement.

Figure 8:
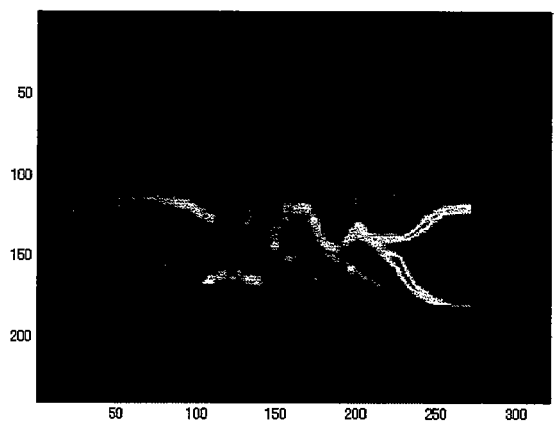
FIGS. 8(A) to 8(D) are diagrams comparing a case where pixel values of a threshold value or less are made zero and a case where they are not made zero in an image after edge enhancement.
Figure 8:
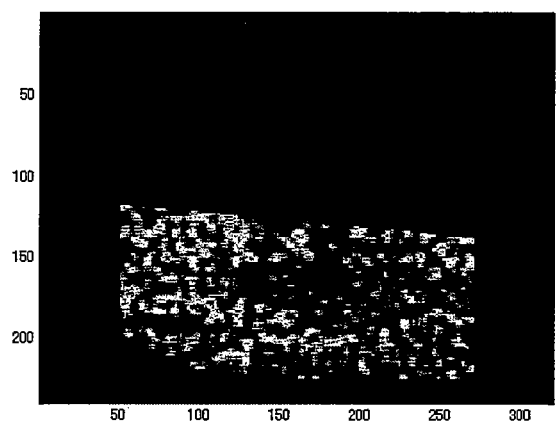
Figure 8:
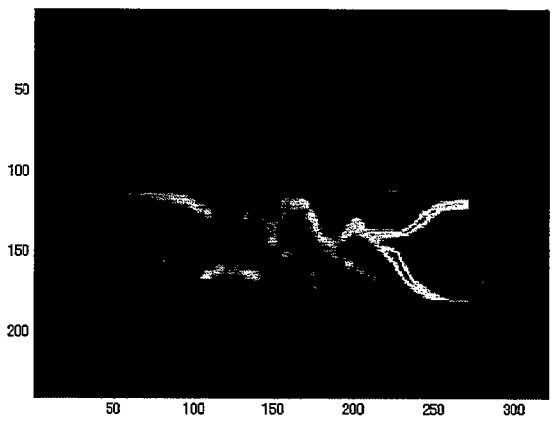
Figure 8:
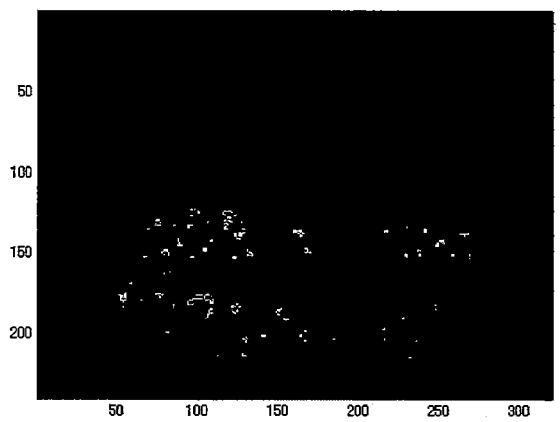

FIGS. 8(A) and 8(B) show images the same as FIGS. 6(C) and 6(D) and show images in the case where the pixel values of the threshold value or less are not made zero.

On the other hand, FIGS. 8(C) and 8(D) show images where all pixel values not more than the threshold value "255" included in images of FIGS. 8(A) and 8(B) are made zero.

When the captured image includes the subject FG, as seen from the comparison of FIGS. 8(A) and 8(C), even when the pixel values of the threshold value or less are made zero, the principal characteristics of the edges (that is, the image of the blood vessels) is maintained. Contrary to this, when the captured image does not include the subject FG, as seen from the comparison of FIGS. 8(B) and 8(D), most of the edges disappear when making the pixel values of the threshold value or less zero, and the characteristics of the edges greatly change.

Figure 9:
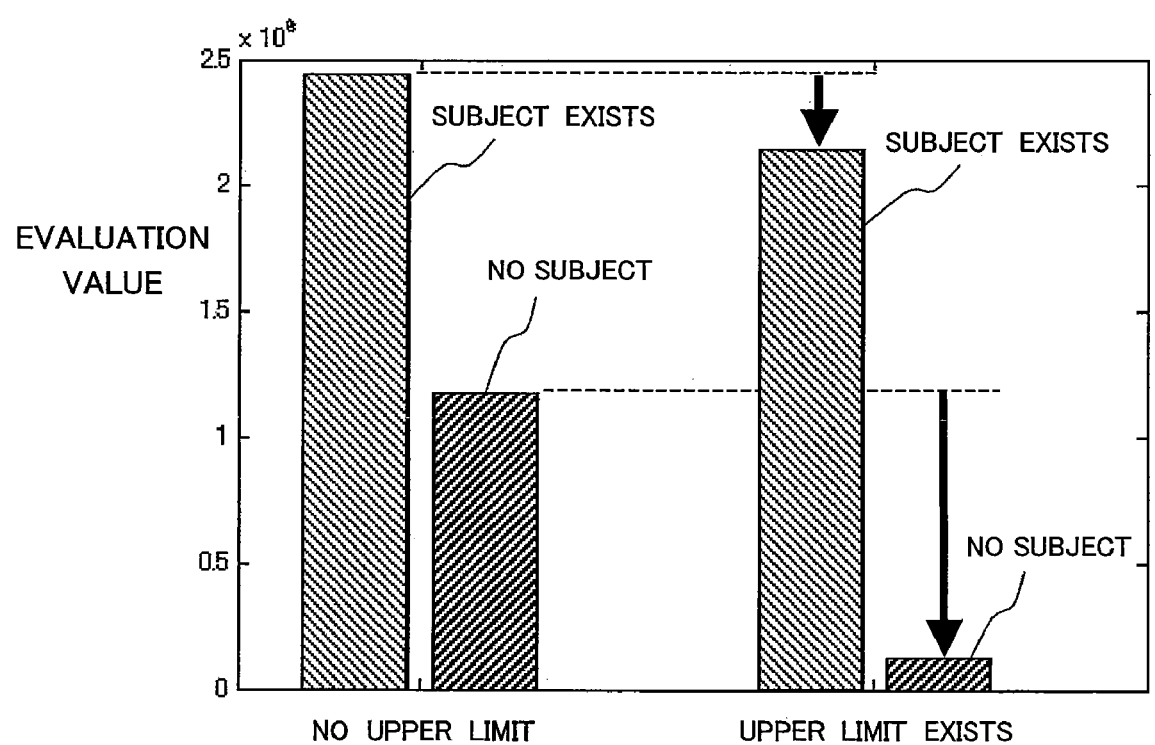
FIG. 9 is a diagram comparing an evaluation value in a case where pixel values of a predetermined threshold value or less are made zero and a case where a threshold value is not provided in the image shown in FIGS. 8(A) to 8(D).

FIG. 9 is a diagram comparing the evaluation value (sum of pixel values) when pixel values not more than the threshold value "255" are made zero in the image shown in FIGS. 8(A) to 8(D) and the evaluation value when the threshold value is not provided.

When the threshold value is not provided, the evaluation value Ev of the image including the subject (FIG. 8(A)) became "2434244", and the evaluation value Ev of the image not including the subject (FIG. 8(B)) became "1177685". Contrary to this, when pixel values of the threshold value "255" or less were made zero, the evaluation value Ev of the image including the subject FG (FIG. 8(C)) became "2145659", and the evaluation value Ev of the image not including the subject FG (FIG. 8(D)) became "117921". As apparent from this FIG. 9, by calculating the evaluation value Ev by eliminating pixel values of the predetermined threshold value or less in the image after the edge enhancement, the difference of evaluation values Ev in accordance with the presence/absence of the subject FG can be made clearer.

The judgment unit 106 judges whether or not the image of the subject FG is included in the image input from the image capturing unit 40 based on the evaluation value Ev acquired in the evaluation value acquisition unit 105.

The judgment unit 106, for example as shown in FIG. 1, has a first judgment unit 1061, second judgment unit 1062, and third judgment unit 1063.

The first judgment unit 1061 compares the evaluation values Ev of images sequentially acquired in the image acquisition unit 101 and a threshold value Td and judges whether or not the intensities of edges and/or amounts of edges included in the acquired images reach the lowest reference level.

When the predetermined number of images judged to reach the first reference level at the first judgment unit 1061 are continuously acquired, the second judgment unit 1062 determines a threshold value Th for determining an intermediate reference level exceeding the above lowest reference level based on the evaluation values Ev of the predetermined number of images. Then, it compares the evaluation value Ev of any one of the predetermined number of images or the image acquired after the predetermined number of images and the threshold value Th and judges whether or not the image compared includes an image of the subject FG based on the comparison result.

The third judgment unit 1063 compares the evaluation values Ev sequentially acquired in the evaluation value acquisition unit 105 and a threshold value Tu for determining the highest reference level exceeding the above intermediate reference level and judges whether or not the image compared includes an image of the subject FG based on the resultant comparison result.

As previously explained, the evaluation value Ev acquired at the evaluation value acquisition unit 105 expresses the characteristic of the image of the subject FG suitable as the template use image. It can be judged whether or not the captured image includes subject FG in accordance with magnitude of this value. Accordingly, the judgment unit 106 may judge whether or not the image compared is registered based on the result of comparing the evaluation value Ev and a single threshold value. However, the following phenomena sometimes occur at the time of actual template registration. Therefore, there is a case where a suitable template cannot be registered by a simple judgment by a single threshold value.

(1) The finger moved at the time of capturing the image;
(2) the image could not be captured so beautifully due to the influence of the exposure etc.; and
(3) the veins of the finger are thin and light.

In the case of (1) and the case of (2), the registration of a template may be possible, but there is a possibility that a template in a worse state than its original state (for example information of blood vessel pattern is small) will be registered. Then, there arises the inconvenience that the comparison will not be possible even though usually the comparison is easily performed or that the comparison will fail. Further, in the case of (3), the threshold value may be too high relative to the evaluation value Ev and the template may not be able to be registered. However, if the threshold value is made too low, the possibility of registering the template in a bad state becomes high.

Therefore, the judgment unit 106 shown in FIG. 1 judges possibility/impossibility of registration by using not a single threshold value, but three threshold values (Td, Tu, Th).

The threshold value Td of the first judgment unit 1061 determines the lowest reference level of the image used for the template. This is set based on the value of the evaluation value Ev obtained when a person having thin and light veins of the finger can be stably captured as in (3) explained above. When the evaluation value Ev is smaller than the threshold value Td, that image is not used for the template.

The threshold value Tu of the third judgment unit 1063 determines the highest reference level of the image used for the template. This is set based on the evaluation value Ev obtained in a case of the image capturing unit 40 stably capturing an image and capturing sufficiently beautiful finger veins. There are individual differences in the thicknesses of the blood vessels, therefore, even when an image can be stably captured, all users may not always be registered by the template passing the highest reference level of the threshold value Tu.

The threshold value Th of the second judgment unit 1062 determines the intermediate reference level exceeding the lowest reference level of the threshold value Td, but not satisfying the highest reference level of the threshold value Td. The threshold value Th is determined based on the evaluation values Ev of the continuously captured images. The threshold values Td and Tu are previously set fixed values, and the threshold value Th is the value changing for each subject and each image capture.

The registration unit 107 extracts the information of the blood vessel pattern from the captured image judged at the first judgment unit 1061 or third judgment unit 1063 to include the image of the subject FG and stores this as the template DAT in the storage unit 70.

The comparison unit 108 extracts the information of the blood vessel pattern from the captured image judged to include the image of the subject FG at the first judgment unit 1061 or the third judgment unit 1063 and compares this extracted information and the template DAT stored in the storage unit 70.

The display processing unit 109 performs the processing for displaying information in accordance with the evaluation values Ev of the images sequentially acquired at the image acquisition unit 101 in the image display unit 50. Further, it performs the processing for displaying the information in accordance with the number of continuous acquisitions of images judged to reach the lowest reference level in the first judgment unit 1061 in the image display unit 50.

The operation of the image processing system shown in FIG. 1 having the configuration explained above will be explained next.

An example of the calculation processing of the evaluation value Ev in the image processing system shown in FIG. 1 will be explained with reference level to the flow chart of FIG. 10.

The image acquisition unit 101 controlling the light source 20 and the image capturing unit 40 to capture an image of the subject FG and thereby acquires a captured image If (step ST101).

The contour detection unit 102 detects the contours of the subject FG included in the image If and prepares a mask Mf for cutting out the inside of the contours. Further, the region specifying unit 103 specifies the region inside from the contours detected at the contour detection unit 102 and prepares a mask eMf for cutting out that inside region (step ST102).

On the other hand, the edge enhancement unit 104 performs the processing for enhancing the edges of the image If. Namely, it eliminates the noise components of the image If by a Gaussian filter (step ST103) and applies a Laplacian filter with respect to an image Gf after this noise elimination to thereby enhance the edge portions (step ST104).

The evaluation value acquisition unit 105 performs the masking for cutting out the inside region specified by the region specifying unit 103 from an image Lf with edges enhanced by the Laplacian filter (step ST105). Then, it makes the pixel values of a threshold value Vunder or less included in an image Of after this masking zero (step ST106) and calculates the sum of the pixel values (step ST107). The computed sum of the pixel values is supplied as the evaluation value Ev to the judgment unit 106.

The above description is the explanation of the calculation processing of the evaluation value Ev.

An example of the template registration processing in the image processing system shown in FIG. 1 will be explained with reference level to the flow chart shown in FIG. 11.

The judgment unit 106 initializes a variable i for entering the number of continuously acquired evaluation values Ev and a variable hEvi (i=0, 1, . . . , n−1) for entering n number of continuously acquired evaluation values Ev (ST201).

Then, the contour detection unit 102, region judgment unit 103, edge enhancement unit 104, and the evaluation value acquisition unit 105 calculate an evaluation value Ev of the captured image If according to the processing of steps ST202 to ST207.

Figure 10:
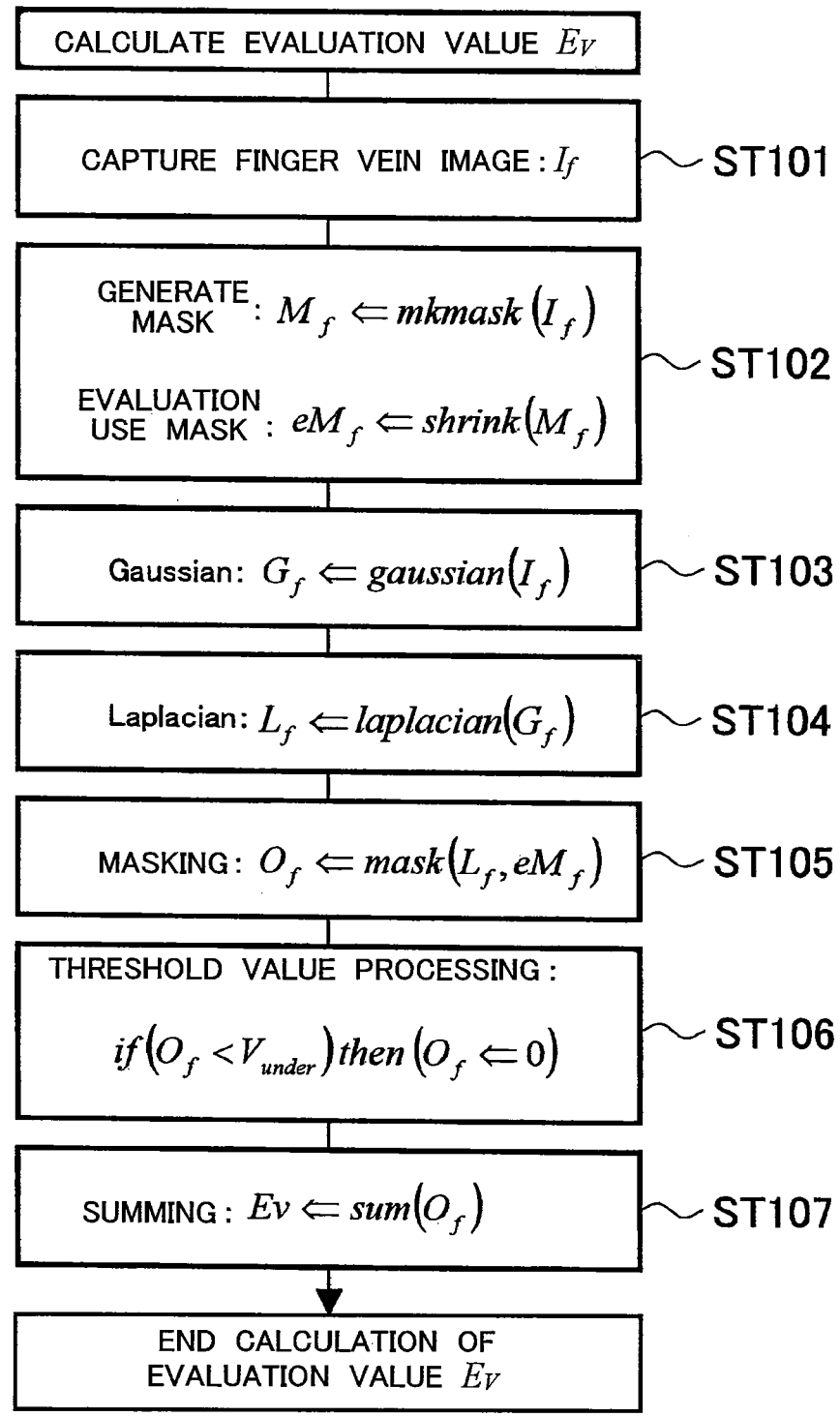
FIG. 10 is a flow chart for explaining an example of calculation of evaluation values in the image processing system shown in FIG. 1.
Figure 11:
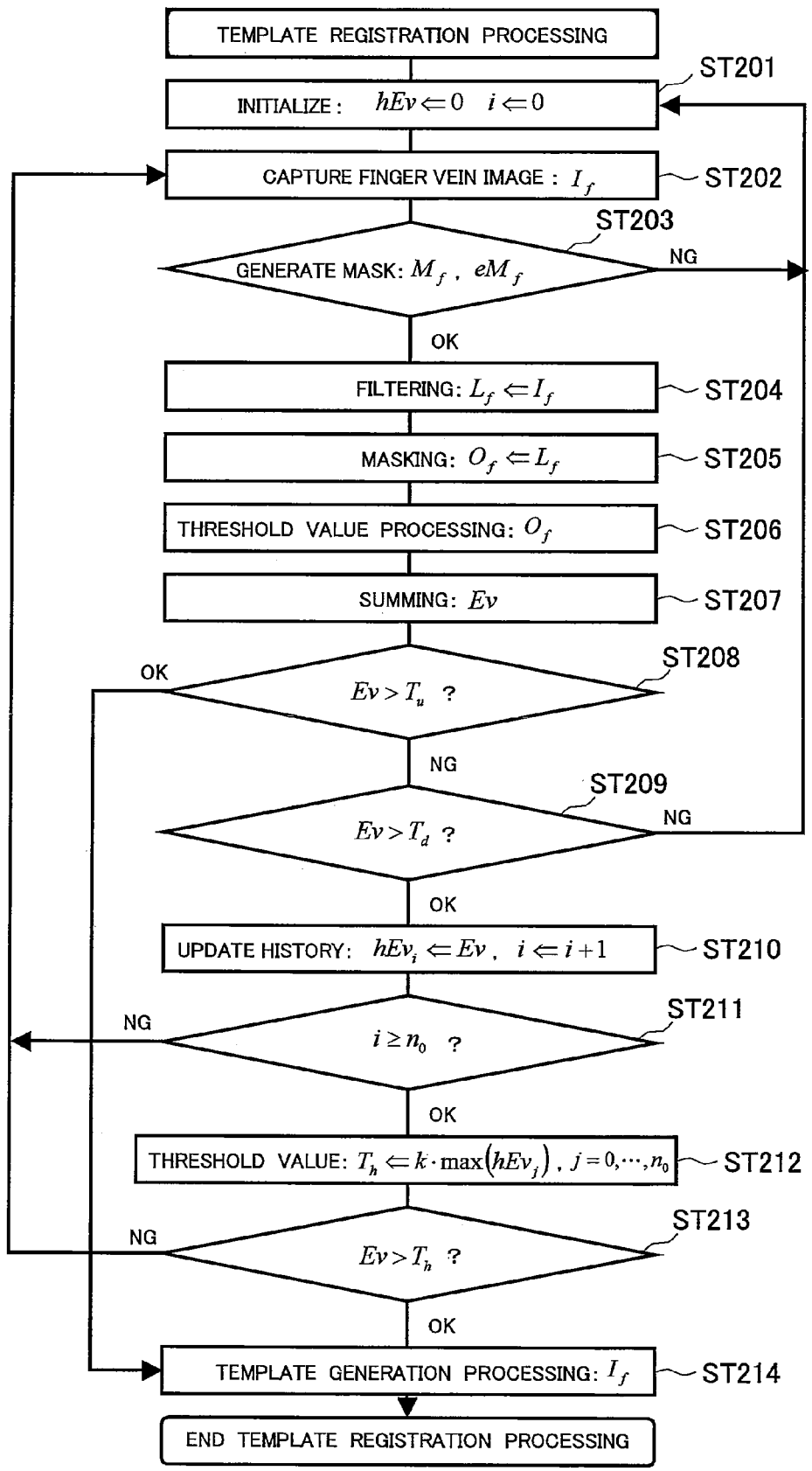
FIG. 11 is a flow chart for explaining an example of template registration in the image processing system shown in FIG. 1.

When comparing FIG. 10 and FIG. 11, step ST202 corresponds to step ST101, step ST203 corresponds to step ST102, step ST204 corresponds to steps ST103 and ST104, step ST205 corresponds to step ST105, step ST206 corresponds to step ST106, and step ST207 corresponds to step ST107.

When the generation of a mask fails in the mask generation processing of step ST203 (for example, where the finger is separated from the device and cannot be captured), the judgment unit 106 returns to step ST201 and initializes the variables i and hEv$_i$. Due to this, when the continuity of the image capture is interrupted, the history of the evaluation values Ev (hEv$_0$, hEv$_1$, . . . hEv$_{n-1}$) is immediately erased, and the recording of new history is started.

When an evaluation value Ev is computed, the third judgment unit 1063 compares this evaluation value Ev and the threshold value Tu and judges whether or not the evaluation value Ev exceeds the highest reference level based on the comparison result (step ST208). Where it is judged that the evaluation value Ev exceeds the highest reference level, the registration unit 107 extracts the information of the blood vessel pattern from the captured image of this evaluation value Ev and stores it as the template DAT in the storage unit 70 (step ST214).

When it is judged in the third judgment unit 1063 that the evaluation value Ev does not satisfy the highest reference level, the first judgment unit 1061 compares this evaluation value Ev and the threshold value Td and judges whether or not the evaluation value Ev exceeds the lowest reference level (step ST209). When it is judged that the evaluation value Ev does not satisfy the lowest reference level (for example a case where the placement of the finger is unsuitable), the judgment unit 106 returns to step ST201 and initializes the variables i and hEv$_i$. Due to this, where the continuity of the image capture is interrupted, the history of the evaluation values Ev (hEv$_0$, hEv$_1$, . . . , hEv$_{n-1}$) is immediately erased, and the recording of new history is started.

When it is judged at the first judgment unit 1061 that the evaluation value Ev exceeds the lowest reference level, the judgment unit 106 enters the evaluation value Ev in the variable hEvi for history and adds "1" to the variable i representing the history number (step ST210).

Then, the judgment unit 106 compares the variable i obtained by adding "1" and a predetermined number n0 (step ST211). When the variable i is smaller than the predetermined number n0, the judgment unit 106 returns the processing to step ST202 (step ST211). Due to this, the processing of steps ST202 to ST207 are executed again, whereby the evaluation value Ev of a new captured image If is calculated.

On the other hand, when the variable i reaches the predetermined number n0, the second judgment unit 1062 determines the threshold value Th based on the (n0+1) evaluation value entered in the variables hEv$_0$, hEv$_1$, . . . , and hEv$_{n0}$. Namely, a number obtained by multiplying the maximum value among (n0+1) evaluation values by a coefficient k (k is larger than 0 and smaller than 1) is determined as the threshold value Th (step ST212). The coefficient k is set to a value of for example about "0.9". It is required to stably acquire a higher evaluation value Ev as the coefficient k approaches "1".

When the threshold value Th is determined at step ST212, next, the second judgment unit 1062 compares the evaluation value Ev and the threshold value Th and judges based on the comparison result whether or not the present evaluation value Ev of the captured image exceeds the intermediate reference level (step ST213). When it is judged at step ST213 that the evaluation value Ev does not reach the intermediate reference level, the judgment unit 106 returns the processing to step ST202 (step ST211). Due to this, the processing of steps ST202 to ST207 is executed again, and the new evaluation value Ev of the captured image If is calculated. On the other hand, when it is judged at step ST213 that the evaluation value Ev reaches the intermediate reference level, the registration unit 107 extracts the information of the blood vessel pattern from the captured image of this evaluation value Ev and stores this as the template DAT in the storage unit 70 (step ST214).

The variables hEv$_0$, hEv$_1$, . . . , and hEv$_{n-1}$ for the storage of history sequentially store the evaluation values Ev until the image for registration of the template is decided so long as the initialization processing of variables (step ST201) is not returned to in the middle. If storing the evaluation values Ev in these variables in a for example FIFO (First In First Out) format, it is possible to keep the history of as much as n number of the values.

The above concludes the explanation of the template registration processing.

An example of display of the image display unit 50 during the execution of the template registration processing explained above will be explained with reference to FIG. 12.

The user cannot judge by himself if the image of his finger captured at present is suitable as a template during the registration of the template. For this reason, the user cannot learn how to tilt or place the finger in order to obtain the suitable captured image unless being provided with some information, therefore, he must continue with trial and error until the system judges the image passes. Therefore, the image processing system according to the present embodiment feeds back the state during the template registration to the user so as to enable smooth acquisition of the template use image.

Figure 12:
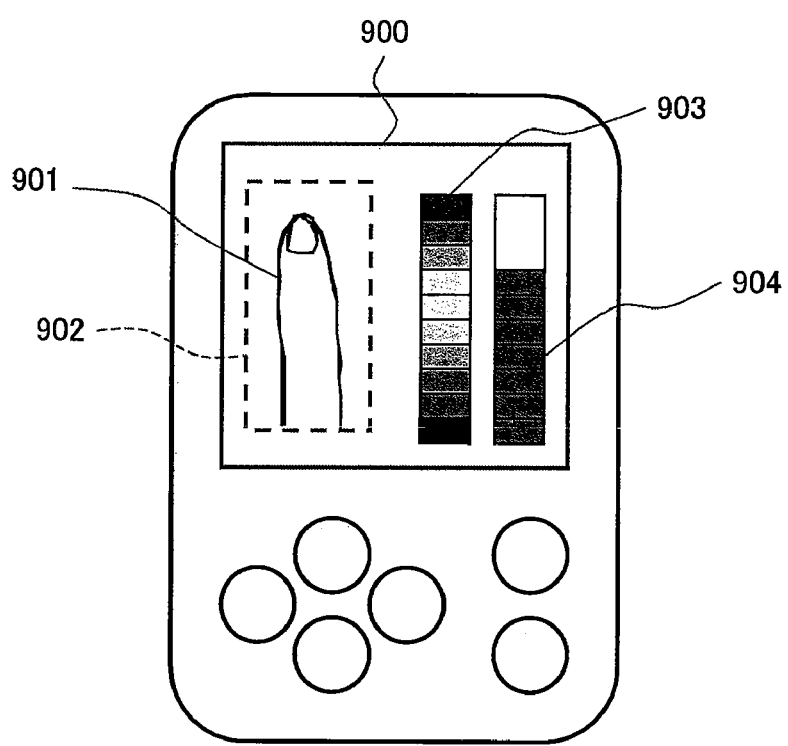
FIG. 12 is a diagram showing an example of display of an image display unit during execution of the template registration.

The display unit 109 makes a screen 900 of the image display unit 50 display for example information concerning the evaluation value Ev of the image. In the example of FIG. 12, the values between the threshold values Td and Tu explained previously are divided into 10 stages. At which stage the evaluation value Ev acquired at present exists is represented by a bar graph 903. Due to this, the user can accurately grasp how the finger should be arranged so as to obtain the suitable image.

Further, the display processing unit 109 makes the screen 900 display information concerning the number of continuous acquisitions of images judged to have evaluation values Ev larger than the threshold value Td (that is, the variable i of FIG. 11). In the example of FIG. 12, the value of the variable i is represented by the bar graph 904. Due to this, the user can grasp how long the present finger arrangement should be held in order to pass the judgment.

Further, the display processing unit 109 makes the screen 900 display information indicating at which position the finger of the user is at with respect to the range where image capture is possible by the image capturing unit 40. In the example of FIG. 12, by arranging a picture 901 representing the finger of the user in the broken line frame 902 representing an image capture range, the position of the finger at present with respect to the image capture range is represented. Due to this, the user can accurately grasp how the finger should be placed in order to obtain the suitable image.

As explained above, according to the present embodiment, the edges of the captured image are enhanced and an evaluation value Ev concerning the intensities and/or amounts of the edges included in the captured image is acquired based on the values of the pixels included in the edge enhanced image. Then, based on the acquired evaluation value Ev, it is judged whether or not the captured image includes an image of the predetermined subject FG. Due to this, whether or not the captured image includes an image of subject FG can be accurately judged without depending upon vague human judgment.

Further, the evaluation value Ev is a value related to the intensities and/or amounts of edges included in a captured image, therefore it is possible to judge according to the value of the evaluation value Ev not only whether or not the captured image includes an image of the subject FG, but also if the image of the subject FG is suitable for a predetermined purpose. For example, in the template registration processing, it is possible to judge not only if the captured image includes the subject FG, but also if that is suitable as a template use image.

Further, according to the present embodiment, the contours of the subject FG included in the captured image are detected, and a region inside from the contours is specified. Then, the evaluation value Ev is acquired based on the values of the pixels included in this specified inside region among all pixels included in the image after the edge enhancement. Due to this, the influence of the edges occurring at the contour portions of the subject FG is effectively eliminated, and an evaluation value Ev correctly reflecting the state of the edges included inside the subject FG can be acquired. For this reason, it is possible to suitably judge if the captured image includes the subject FG and if that subject FG is suitable for a predetermined purpose (for template) in accordance with the characteristics of the for example blood vessel pattern or other image included inside the subject FG.

Further, according to the present embodiment, the evaluation values Ev of sequentially captured images and the threshold value Td are compared, and it is sequentially judged based on the comparison results if the intensities and/or amounts of edges included in the captured images reach the lowest reference level. Then, when a predetermined number of images judged to reach the lowest reference level are continuously acquired, the threshold value Th for determining the intermediate reference level exceeding the lowest reference level is determined based on the evaluation values Ev of the predetermined number of images. When the threshold value Th is determined, the evaluation value Ev of any one of the predetermined number of images or an image acquired after the predetermined number of images and the threshold value Th are compared, and it is judged based on the comparison result whether or not the image compared includes an image of the subject FG.

Namely, unless the intensities and/or amounts of edges included in a series of captured images stably exceed the predetermined lowest reference level, it is not judged that the series of captured images includes an image of the subject FG. Due to this, it is possible to prevent it being judged that the captured image includes the subject FG when the subject moves during image capture, when the exposure and other conditions are not suitable for the brightness of the background, or otherwise when the image capturing conditions are unstable, so the reliability of the judgment results can be raised.

Further, the threshold value Th of the intermediate reference level exceeding the lowest reference level is set based on the evaluation values Ev of a series of captured images, therefore, even in a case where the characteristics of the subjects FG (characteristics of the blood vessel patterns) are different in various ways for each subject, a judgment reference level exceeding the above lowest reference level can be set for each subject. Due to this, in comparison with the case where a fixed reference level is uniformly determined, it becomes possible to perform a suitable judgment in accordance with the difference of the subjects. Further, in the template registration processing, a suitable template can be acquired for each subject.

In addition, according to the present embodiment, the evaluation values Ev of sequentially captured images and the threshold value Tu for determining the highest reference level exceeding the above intermediate reference level are compared, and it is sequentially judged if the image compared includes an image of the subject FG based on the related comparison results.

Namely, the captured image having an evaluation value Ev exceeding the highest reference level is immediately judged as an image including the subject FG, therefore an increase of the speed of the judgment processing can be achieved.

Further, in the present embodiment, information concerning evaluation values Ev of sequentially captured images, information concerning the number of continuous acquisitions of images judged to reach the threshold value Td, or other information concerning the state of the image of the subject FG in each captured image is displayed in the image display unit 50 with each instant.

Due to this, it becomes possible for the user himself to adjust the image capturing conditions (arrangement of subject FG and so on) so that the image of the subject FG included in the captured image becomes a suitable state, therefore the image of the desired subject FG can be more smoothly captured.

Above, the embodiments of the present invention were explained, but the present invention is not limited to only the above embodiments and includes various variations.

In the embodiments explained above, the region specifying unit 103 narrows the contours of the subject FG to the inside by exactly a predetermined distance, but this distance is not limited to a fixed value, but may be changed in accordance with a width of the contours.

For example, in FIG. 4(B), the region specifying unit 103 moves the upper and lower sides of the contours along a line in a vertical direction of the image and moves the left and right sides of the contours along a line in a horizontal direction. At this time, the distance of movement of each pixel located on each side may be set in accordance with the width of the contours in the movement direction thereof.

When explaining this in more detail, the region specifying unit 103 sets the distances of movement of two pixels located at two points in accordance with the distance of these two points at which the line extended in the vertical direction and the contours cross. This movement distance is set so as to become a constant ratio (10% etc.) with respect to the distance of the two points. Then, the pixel on the upper side between the two pixels is moved in the downward direction, and the pixel on the lower side is moved in the upward direction by exactly a set movement distance. This is true also for pixels forming the left and right sides of the contours. Movement distances of two pixels located at these two points are set in accordance with the distance of two points at which the line extended in the horizontal direction and the contours cross. Then, between the two pixels, the pixel on the left side moves in the rightward direction, and the pixel on the right side is moved in the leftward direction by exactly the set movement distances.

In this way, when the distance when narrowing the contours to the inside is set for each pixel in accordance with the width of the contours, even in the case when the subject FG is very small due to individual differences, the region specified by the region specifying unit 103 becoming extremely narrow can be prevented.

Further, in the above embodiments, the contours of the subject FG are comprised of four sides, but the present invention is not limited to this. The contours of the subject FG may be any shape. Namely, the region specifying unit 103 can specify the region inside from the contours no matter what the shape of the contours of the subject FG.

For example, the region specifying unit 103 moves the contours detected at the contour detection unit 102 in the upward direction, downward direction, rightward direction, and leftward direction of the image by exactly predetermined distances. Then, it specifies a region commonly included inside the contours after the movement in directions as a region inside from the contours of the subject FG. The movement distance of the contours in this case may be set at a fixed value in the same way as the example explained above, or may be set in accordance with the width of the contours for each pixel.

In the embodiments explained above, the evaluation value Ev is calculated as the sum of pixel values in the image after applying the edge enhancement and masking, but the present invention is not limited to this.

For example, the evaluation value acquisition unit 105 may acquire the evaluation value Ev based on the number of pixels having edge intensities exceeding the predetermined threshold value among all pixels included in the image with edges enhanced by the edge enhancement unit 104. As seen also from the distribution diagram of FIG. 7, an image including the subject FG includes a lot of strong edges in comparison with an image not including the subject FG. For this reason, in images after edge enhancement and masking, even when the number of pixels having pixel values larger than a certain threshold value (that is pixels having edge intensities exceeding the predetermined threshold value) is acquired as the evaluation value Ev, it is possible to judge presence/absence of the subject FG with a high precision.

Further, the evaluation value acquisition unit 105 may acquire the evaluation value Ev based on the value of the pixel having the highest edge intensity among all pixels included in the image with edges enhanced in the edge enhancement unit 104. When giving a concrete example, the maximum value of the pixel values becomes "2257" in the image shown in FIG. 6(C), and the maximum value of the pixel values becomes "428" in the image shown in FIG. 6(D). When the influence of the contours of the subject FG is sufficiently eliminated by the masking by the contour detection unit 102 and the region specifying unit 103, as in the example described above, a large difference occurs in the maximum values of pixel values in accordance with presence/absence of the subject FG. Accordingly, even when the evaluation value Ev is simply acquired based on the maximum value of pixel values (that is the value of pixel having the highest edge intensity), it is possible to judge presence/absence of the subject FG with a high precision.

In the above embodiments, the example of judging whether or not a captured image suitable for the registration of a template is obtained by using the evaluation value is explained, but the present invention is not limited to this. For example, before performing the comparison between the captured image and the template, it may be judged whether or not a captured image suitable for the comparison is obtained, and the comparison processing may be executed limited to the case where that captured image is obtained. Due to this, useless comparison is no longer executed, therefore the power consumption can be reduced.

The control unit 10 may be realized by software by a computer as in the above embodiments or at least a portion thereof may be realized by hardware such as a signal processing circuit.

In the above embodiments, the example of applying the present invention to biometric authentication (template registration, comparison, etc.) was explained, but the present invention is not limited to this. Namely, the present invention can be widely applied to various image processing in which it is necessary to distinguish the image of a subject including edges in the inside and a plain background.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An image processing system comprising:
    an edge enhancement unit configured to enhance edges of an image,
    a contour detection unit configured to detect contours from said image,
    a region specifying unit configured to specify a region inside the contours detected at said contour detection unit,
    an evaluation value acquisition unit configured to acquire an evaluation value concerning intensities of edges and/or amounts of edges included in said image based on values of pixels included in the region specified at said region specifying unit in the image with edges enhanced at said edge enhancement unit, and a judgment unit configured to judge whether or not said image includes an image of a predetermined subject to be captured as the image based on the evaluation value acquired by said evaluation value acquisition unit.

2. An image processing system as set forth in claim 1, wherein said evaluation value acquisition unit acquires said evaluation value based on a sum of values of all pixels included in the region specified at said region specifying unit in the image with edges enhanced at said edge enhancement unit.

3. An image processing system as set forth in claim 1, wherein said evaluation value acquisition unit acquires said evaluation value based on the sum of values of pixels having intensities of edges exceeding a predetermined threshold value among all pixels included in the region specified at said region specifying unit in the image with edges enhanced at said edge enhancement unit.

4. An image processing system as set forth in claim 1, wherein said evaluation value acquisition unit acquires said evaluation value based on a number of pixels having intensities of edges exceeding a predetermined threshold value among all pixels included in the region specified at said region specifying unit in the image with edges enhanced at said edge enhancement unit.

5. An image processing system as set forth in claim 1, wherein said evaluation value acquisition unit acquires said evaluation value based on the value of the pixel having the highest edge intensity among all pixels included in the region specified at said region specifying unit in the image with edges enhanced at said edge enhancement unit.

6. An image processing system as set forth in claim 1, wherein said region specifying unit makes contours detected at said contour detection unit move in a predetermined plurality of directions set on a plane of said image by exactly predetermined distances and specifies a region commonly included inside contours after the movement in the different directions as the region inside from the contours of said subject in that case.

7. An image processing system as set forth in claim 6, wherein said region specifying unit sets a movement distance of said contours in accordance with a distance of two points at which a straight line running along a movement direction and said contours cross for each pixel on said contours.

8. An image processing system as set forth in claim 1, wherein said system comprises an image acquisition unit configured to sequentially acquire said images, said edge enhancement unit sequentially enhances edges of said images acquired at said image acquisition unit, and said evaluation value acquisition unit sequentially acquires evaluation values of images acquired at said image acquisition unit, said judgment unit including:

a first judgment unit for comparing evaluation values of images sequentially acquired at said image acquisition unit and a first threshold value and judging whether or not intensities of edges and/or amounts of edges included in said acquired images reach a first reference level based on the comparison results; and a second judgment unit for determining a second threshold value for determining a second reference level exceeding said first reference level based on evaluation values of a predetermined number of images judged to reach said first reference level in said first judgment unit when the predetermined number of images are continuously acquired, comparing the evaluation value of any one of the predetermined number of images or an image acquired following the predetermined number of images and said second threshold value, and judging whether or not the image compared includes an image of said subject based on the comparison result.

9. An image processing system as set forth in claim 8, wherein said judgment unit includes a third judgment unit configured to compare evaluation values sequentially acquired at said evaluation value acquisition unit and a third threshold value for determining a third reference level exceeding said second reference level and judge whether or not the image compared includes an image of said subject based on the comparison result.

10. An image processing system as set forth in claim 8, further comprising an information output unit configured to output information concerning the evaluation values of images sequentially acquired at said image acquisition unit.

11. An image processing system as set forth in claim 8, further comprising an information output unit configured to output information in accordance with the number of continuously acquired images judged to reach said first reference level at said first judgment unit.

12. An image judgment method for judging whether or not an image includes an image of a predetermined subject to be captured as the image, said image judgment method including:

a first step of enhancing the edges of said image, a second step of detecting the contours of said subject from said image, a third step of specifying a region inside the contours detected in said second step, a fourth step of acquiring an evaluation value concerning intensities and/or amounts of edges included in said image based on values of pixels included in the region specified in said third step in the image with edges enhanced in said first step, and a fifth step of judging whether or not the image includes an image of said subject based on the evaluation value acquired in said fourth step.

13. An image judgment method as set forth in claim 12, further including a sixth step of sequentially acquiring images, said first step sequentially enhancing edges of said images acquired in said sixth step, said fourth step sequentially acquiring evaluation values of said images acquired in said sixth step, and said fifth step including;

a seventh step of comparing evaluation values of said images sequentially acquired in said sixth step and a first threshold value and judging whether or not intensities of edges and/or amounts of edges included in said acquired images reach a first reference level based on the comparison results, and an eighth step of determining a second threshold value determining a second reference level exceeding said first reference level based on evaluation values of a predetermined number of images judged to reach said first reference level in said seventh step when said predetermined number of images are continuously acquired, comparing the evaluation value of any one of the predetermined number of images or an image acquired after the predetermined number of images and said second threshold value, and judging whether or not the image compared includes an image of said subject based on the comparison result.

14. A non-transitory computer readable medium storing a program for making an image processing system including a computer for judging whether or not an image includes an image of a predetermined subject to be captured as the image, perform:
- a first step of enhancing edges of said image,
- a second step of detecting the contours of said subject from said image,
- a third step of specifying a region inside from the contours detected in said second step,
- a fourth step of acquiring an evaluation value concerning intensities of edges and/or amounts of edges included in said image based on values of pixels included in the region specified in said third step in the image with edges enhanced in said first step, and
- a fifth step of judging whether or not the image includes an image of said subject based on the evaluation value acquired in said fourth step.

15. A non-transitory computer readable medium storing a program as set forth in claim 14, further
- making said image processing system execute a sixth step of sequentially acquiring images,
- said first step sequentially enhancing edges of said images acquired in said sixth step,
- said fourth step sequentially acquiring evaluation values of said images acquired in said sixth step, and
- said fifth step including:
- a seventh step of comparing evaluation values of said images sequentially acquired in said sixth step and a first threshold value and judging whether or not intensities of edges and/or amounts of edges included in said acquired images reach a first reference level based on the comparison results, and
- an eighth step of determining a second threshold value determining a second reference level exceeding said first reference level based on evaluation values of a predetermined number of images judged to reach said first reference level in said seventh step when said predetermined number of images are continuously acquired, comparing the evaluation value of any one of the predetermined number of images or an image acquired after the predetermined number of images and said second threshold value, and judging whether or not the image compared includes an image of said subject based on the comparison result.

16. An image processing system comprising:
- an edge enhancement means for enhancing edges of an image,
- a contour detection means for detecting contours of said subject from said image,
- a region specifying means for specifying a region inside the contours detected at said contour detecting means,
- an evaluation value acquiring means for acquiring an evaluation value concerning intensities of edges and/or amounts of edges included in said image based on values of pixels included in the region specified at said region specifying means in the image with edges enhanced at said edge enhancement means, and
- a judging means for judging whether or not said image includes an image of a predetermined subject to be captured as the image based on the evaluation value acquired by said evaluation value acquiring means.

17. An image processing system as set forth in claim 16, wherein
- said system further comprises an image acquiring means for sequentially acquiring said images,
- said edge enhancement means sequentially enhances edges of said images acquired at said image acquiring means, and
- said evaluation value acquiring means sequentially acquires evaluation values of images acquired at said image acquiring means, and
- said judging means includes:
- a first judging means for comparing evaluation values of images sequentially acquired at said image acquiring means and a first threshold value and judging whether or not intensities of edges and/or amounts of edges included in said acquired images reach a first reference level based on the comparison results, and
- a second judging means for determining a second threshold value for determining a second reference level exceeding said first reference level based on evaluation values of a predetermined number of images judged to reach said first reference level in said first judging means when the predetermined number of images are continuously acquired, comparing the evaluation value of any one of the predetermined number of images or an image acquired following the predetermined number of images and said second threshold value, and judging whether or not the image compared includes an image of said subject based on the comparison result.

18. An image processing system as set forth in claim 17, wherein said judging means comprises a third judging means for comparing evaluation values sequentially acquired at said evaluation value acquiring means and a third threshold value for determining a third reference level exceeding said second reference level and judge whether or not the image compared includes an image of said subject based on the comparison result.

19. An image processing system as set forth in claim 17, further comprising an information outputting means for outputting information concerning the evaluation values of images sequentially acquired at said image acquiring means.

20. An image processing system as set forth in claim 17, further comprising an information outputting means for outputting information in accordance with the number of continuously acquired images judged to reach said first reference level at said first judging means.

* * * * *

UNITED STATES PATENT AND TRADEMARK OFFICE
CERTIFICATE OF CORRECTION

Page 1 of 1

PATENT NO. : 7,912,293 B2
APPLICATION NO. : 11/577903
DATED : March 22, 2011
INVENTOR(S) : Hiroshi Abe It is certified that error appears in the above-identified patent and that said Letters Patent is hereby corrected as shown below:

On the face of the patent, add:

Foreign Application Priority Data
Sep. 6, 2005 (JP).......................P2005-257858

Signed and Sealed this
Twenty-second Day of November, 2011

David J. Kappos
*Director of the United States Patent and Trademark Office*